United States Patent
Yu et al.

(12) 
(10) Patent No.: US 6,737,563 B2
(45) Date of Patent: May 18, 2004

(54) TRANSGENIC SEEDS EXPRESSING AMYLOPULLULANASE AND USES THEREFOR

(75) Inventors: Su-May Yu, Taipei (TW); Jei-Fu Shaw, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/050,763

(22) Filed: Jan. 16, 2002

(65) Prior Publication Data

US 2003/0135884 A1 Jul. 17, 2003

(51) Int. Cl.[7] ................ C12N 15/82; C12N 15/31; C12N 15/56; A01H 5/00; C12P 19/04
(52) U.S. Cl. ................ 800/284; 800/278; 800/287; 800/288; 800/320; 800/320.1; 800/320.2; 800/320.3; 435/69.8; 435/101; 435/202; 435/210
(58) Field of Search .................. 800/278, 284, 800/287, 288, 320, 320.1, 320.2, 320.3; 435/69.8, 101, 202, 210

(56) References Cited

U.S. PATENT DOCUMENTS

| | | | |
|---|---|---|---|
| 5,516,668 A | * | 5/1996 | Maruta ............ 435/172.3 |
| 5,750,876 A | * | 5/1998 | Barry et al. ............ 800/205 |
| 5,888,789 A | * | 3/1999 | Rodriguez ............ 435/172.3 |
| 6,043,074 A | * | 3/2000 | Duffner ............ 435/200 |

FOREIGN PATENT DOCUMENTS

EP 1164194 * 12/2001

OTHER PUBLICATIONS

Ramesh et al. Appl. Environ. Microbiol. 60(1): 94–101, Feb. 1994.*
Kossmann et al, pp. 271–278 In: Carbohydrate Bioengineering, Petersen et al, eds., Elsevier: Amsterdam, 1995.*
Leisy et al. Plant Mol. Biol. 14(1): 41–50, 1989.*
Zeilous et al. pp. 253–262 In: Recent Adv. Carbohydrate Bioeng., vol. 246, Royal Soc. Chem., 1999.*
Chiang et al. Amer. Soc. Plant Biol., Meeting Posters Jul. 21–Jul. 25, 2001, Abs. # 567, Jul. 2001.*
Mathupala et al. J. Biol. Chem. 268(22): 16332–16344, Aug. 1993.*

* cited by examiner

*Primary Examiner*—David T. Fox
(74) *Attorney, Agent, or Firm*—Fish & Richardson P.C.

(57) ABSTRACT

The invention provides DNA constructs and genetically engineered seeds for the expression of amylopullulanase in plant seeds such as rice seeds. Related methods are also provided for the production of sugars, modified starches, and high protein products, and use of the glutelin promoter in the methods.

33 Claims, 1 Drawing Sheet

A. pGApu

B. pGpApu

C. pA3Apu

D. pA8Apu

SEQUENCE LISTING

```
<160> NUMBER OF SEQ ID NOS: 13

<210> SEQ ID NO 1
<211> LENGTH: 1481
<212> TYPE: PRT
<213> ORGANISM: Thermoana  ethanolicus

<400> SEQUENCE: 1

Met Phe Lys Arg Arg Thr Leu Gly Phe Leu Leu Ser Phe Leu Leu Ile
 1               5                  10                  15

Tyr Thr Ala Val Phe Gly Ser Met Pro Val Gln Phe Ala Lys Ala Glu
            20                  25                  30

Thr Asp Thr Ala Pro Ala Ile Ala Asn Val Val Gly Asp Phe Gln Ser
        35                  40                  45

Lys Ile Gly Asp Ser Asp Trp Asn Ile Asn Ser Asp Lys Thr Val Met
    50                  55                  60
```

```
Thr Tyr Lys Gly Asn Gly Phe Tyr Glu Phe Thr Thr Pro Val Ala Leu
 65                  70                  75                  80

Pro Ala Gly Asp Tyr Glu Tyr Lys Val Ala Leu Asn His Ser Trp Glu
                 85                  90                  95

Gly Gly Gly Val Pro Ser Gln Gly Asn Leu Ser Leu His Leu Asp Ser
            100                 105                 110

Asp Ser Val Val Thr Phe Tyr Tyr Asn Tyr Asn Thr Ser Ser Val Thr
            115                 120                 125

Asp Ser Thr Lys Tyr Thr Pro Ile Pro Glu Glu Lys Leu Pro Arg Ile
130                 135                 140

Val Gly Thr Ile Gln Ser Ala Ile Gly Ala Gly Asp Trp Lys Pro
145                 150                 155                 160

Glu Thr Ser Thr Ala Ile Met Arg Asp Tyr Lys Phe Asn Asn Val Tyr
                165                 170                 175

Glu Tyr Thr Ala Asn Val Pro Lys Arg Tyr Tyr Glu Phe Lys Val Thr
                180                 185                 190

Leu Gly Pro Ser Trp Asp Ile Asn Tyr Gly Leu Asn Gly Glu Gln Asn
                195                 200                 205

Gly Pro Asn Ile Pro Leu Asn Val Ala Tyr Asp Thr Lys Ile Thr Phe
            210                 215                 220

Tyr Tyr Asp Ser Val Ser His Asn Ile Trp Thr Asp Tyr Asn Pro Pro
225                 230                 235                 240

Leu Thr Gly Pro Asp Asn Asn Ile Tyr Tyr Asp Asp Leu Lys His Asp
                245                 250                 255

Thr His Asp Pro Phe Phe Arg Phe Ala Phe Gly Ala Ile Lys Thr Gly
                260                 265                 270

Asp Thr Val Thr Leu Arg Ile Gln Ala Lys Asn His Asp Leu Glu Ser
            275                 280                 285

Ala Lys Ile Ser Tyr Trp Asp Asp Ile Lys Lys Thr Arg Thr Glu Val
            290                 295                 300

Pro Met Tyr Lys Ile Gly Gln Ser Pro Asp Gly Gln Tyr Glu Tyr Trp
305                 310                 315                 320

Glu Val Lys Leu Ser Phe Asp Tyr Pro Thr Arg Ile Trp Tyr Tyr Phe
                325                 330                 335

Ile Leu Lys Asp Gly Thr Lys Thr Ala Tyr Tyr Gly Asp Asn Asp Glu
            340                 345                 350

Gln Leu Gly Gly Val Gly Lys Ala Thr Asp Thr Val Asn Lys Asp Phe
            355                 360                 365

Glu Leu Thr Val Tyr Asp Lys Asn Leu Asp Thr Pro Asp Trp Met Lys
370                 375                 380

Gly Ala Val Met Tyr Gln Ile Phe Pro Asp Arg Phe Tyr Asn Gly Asp
385                 390                 395                 400

Pro Leu Asn Asp Arg Leu Lys Glu Tyr Ser Arg Gly Phe Asp Pro Val
                405                 410                 415

Glu Tyr His Asp Asp Trp Tyr Asp Leu Pro Asp Asn Pro Asn Asp Lys
                420                 425                 430

Asp Lys Pro Gly Tyr Thr Gly Asp Gly Ile Trp Asn Asn Asp Phe Phe
            435                 440                 445

Gly Gly Asp Leu Gln Gly Ile Asn Asp Lys Leu Asp Tyr Leu Lys Asn
            450                 455                 460

Leu Gly Ile Ser Val Ile Tyr Leu Asn Pro Ile Phe Gln Ser Pro Ser
465                 470                 475                 480

Asn His Arg Tyr Asp Thr Thr Asp Tyr Thr Lys Ile Asp Glu Leu Leu
```

```
                      485                  490                    495
Gly Asp Leu Asp Thr Phe Lys Thr Leu Met Lys Glu Ala His Ala Arg
                500                   505                 510
Gly Ile Lys Val Ile Leu Asp Gly Val Phe Asn His Thr Ser Asp Asp
                515                   520                 525
Ser Ile Tyr Phe Asp Arg Tyr Gly Lys Tyr Leu Asp Asn Glu Leu Gly
                530                   535                 540
Ala Tyr Gln Ala Trp Lys Gln Gly Asp Gln Ser Lys Ser Pro Tyr Gly
545                   550                   555                 560
Asp Trp Tyr Glu Ile Lys Pro Asp Gly Thr Tyr Glu Gly Trp Trp Gly
                        565                 570                 575
Phe Asp Ser Leu Pro Val Ile Arg Gln Ile Asn Gly Ser Glu Tyr Asn
                580                   585                 590
Val Lys Ser Trp Ala Asp Phe Ile Ile Asn Asn Pro Asn Ala Ile Ser
                595                   600                 605
Lys Tyr Trp Leu Asn Pro Asp Gly Asp Lys Asp Ala Gly Ala Asp Gly
                610                   615                 620
Trp Arg Leu Asp Val Ala Asn Glu Ile Ala His Asp Phe Trp Val His
625                   630                   635                 640
Phe Arg Ala Ala Ile Asn Thr Val Lys Pro Asn Ala Pro Met Ile Ala
                        645                 650                 655
Glu Leu Trp Gly Asp Ala Ser Leu Asp Leu Leu Gly Asp Ser Phe Asn
                        660                 665                 670
Ser Val Met Asn Tyr Leu Phe Arg Asn Ala Val Ile Asp Phe Ile Leu
                        675                 680                 685
Asp Lys Gln Phe Asp Asp Gly Asn Val Val His Asn Pro Ile Asp Ala
                690                   695                 700
Ala Lys Leu Asp Gln Arg Leu Met Ser Ile Tyr Glu Arg Tyr Pro Leu
705                   710                   715                 720
Pro Val Phe Tyr Ser Thr Met Asn Leu Leu Gly Ser His Asp Thr Met
                        725                 730                 735
Arg Ile Leu Thr Val Phe Gly Tyr Asn Ser Ala Asn Glu Asn Gln Asn
                740                   745                 750
Ser Gln Glu Ala Lys Asp Leu Ala Val Lys Arg Leu Lys Leu Ala Ala
                755                   760                 765
Ile Leu Gln Met Gly Tyr Pro Gly Met Pro Ser Ile Tyr Tyr Gly Asp
770                   775                   780
Glu Ala Gly Gln Ser Gly Gly Lys Asp Pro Asp Asn Arg Arg Thr Phe
785                   790                   795                 800
Ser Trp Gly Arg Glu Asp Lys Asp Leu Gln Asp Phe Phe Lys Lys Val
                        805                 810                 815
Val Asn Ile Arg Asn Glu Asn Gln Val Leu Lys Thr Gly Asp Leu Glu
                820                   825                 830
Thr Leu Tyr Ala Asn Gly Asp Val Tyr Ala Phe Gly Arg Arg Ile Ile
                835                   840                 845
Asn Gly Lys Asp Val Phe Gly Asn Ser Tyr Pro Asp Ser Val Ala Ile
                850                   855                 860
Val Val Ile Asn Lys Gly Glu Ala Lys Ser Val Gln Ile Asp Thr Thr
865                   870                   875                 880
Lys Phe Val Arg Asp Gly Val Ala Phe Thr Asp Ala Leu Ser Gly Lys
                        885                 890                 895
Thr Tyr Thr Val Arg Asp Gly Gln Ile Val Val Glu Val Val Ala Leu
                900                   905                 910
```

-continued

```
Asp Gly Ala Ile Leu Ile Ser Asp Pro Gly Gln Asn Leu Thr Ala Pro
            915                 920                 925
Gln Pro Ile Thr Asp Leu Lys Ala Val Ser Gly Asn Gly Gln Val Asp
            930                 935                 940
Leu Ser Trp Ser Ala Val Asp Arg Ala Val Ser Tyr Asn Ile Tyr Arg
945                 950                 955                 960
Ser Thr Val Lys Gly Gly Leu Tyr Glu Lys Ile Ala Ser Asn Val Thr
                    965                 970                 975
Gln Ile Thr Tyr Ile Asp Thr Val Thr Asn Gly Leu Lys Tyr Val
                980                 985                 990
Tyr Ser Val Thr Ala Val Asp Ser Asp Gly Asn Glu Ser Ala Leu Ser
            995                 1000                1005
Asn Glu Val Glu Ala Tyr Pro Ala Phe Ser Ile Gly Trp Ala Gly Asn
    1010                1015                1020
Met Asn Gln Val Asp Thr His Val Ile Gly Val Asn Asn Pro Val Glu
1025                1030                1035                1040
Val Tyr Ala Glu Ile Trp Ala Glu Gly Leu Thr Asp Lys Pro Gly Gln
                    1045                1050                1055
Gly Glu Asn Met Ile Ala Gln Leu Gly Tyr Arg Tyr Ile Gly Asp Gly
            1060                1065                1070
Gly Gln Asp Ala Thr Arg Asn Lys Val Glu Gly Val Glu Ile Asn Lys
            1075                1080                1085
Asp Trp Thr Trp Val Asp Ala Arg Tyr Val Gly Asp Ser Gly Asn Asn
            1090                1095                1100
Asp Lys Tyr Met Ala Lys Phe Val Pro Asp Met Val Gly Thr Trp Glu
1105                1110                1115                1120
Tyr Ile Met Arg Phe Ser Ser Asn Gln Gly Gln Asp Trp Thr Tyr Thr
                    1125                1130                1135
Lys Gly Pro Asp Gly Lys Thr Asp Glu Ala Lys Gln Phe Ile Val Val
            1140                1145                1150
Pro Ser Asn Asp Val Glu Pro Pro Thr Ala Leu Gly Leu Gln Gln Pro
            1155                1160                1165
Gly Ile Glu Ser Ser Arg Val Thr Leu Asn Trp Ser Leu Ser Thr Asp
    1170                1175                1180
Asn Val Ala Ile Tyr Gly Tyr Glu Ile Tyr Lys Ser Leu Ser Glu Thr
1185                1190                1195                1200
Gly Pro Phe Val Lys Ile Ala Thr Val Ala Asp Thr Val Tyr Asn Tyr
            1205                1210                1215
Val Asp Thr Asp Val Val Asn Gly Lys Val Tyr Tyr Lys Val Val
            1220                1225                1230
Ala Val Asp Thr Ser Phe Asn Arg Thr Ala Ser Asn Ile Val Lys Ala
            1235                1240                1245
Thr Pro Asp Ile Ile Pro Ile Lys Val Ile Phe Asn Val Thr Val Pro
            1250                1255                1260
Asp Tyr Thr Pro Asp Asp Gly Ala Asn Ile Ala Gly Asn Phe His Asp
1265                1270                1275                1280
Ala Phe Trp Asn Pro Ser Ala His Gln Met Thr Lys Thr Gly Pro Asn
                    1285                1290                1295
Thr Tyr Ser Ile Thr Leu Thr Leu Asn Glu Gly Thr Gln Leu Glu Tyr
            1300                1305                1310
Lys Tyr Ala Arg Gly Ser Trp Asp Lys Val Glu Lys Gly Glu Tyr Gly
            1315                1320                1325
```

```
Glu Glu Ile Ala Asn Arg Lys Ile Thr Val Val Asn Gln Gly Ser Asn
    1330                1335                1340

Thr Met Val Val Asn Asp Thr Val Gln Arg Trp Arg Asp Leu Pro Ile
1345                1350                1355                1360

Tyr Ile Tyr Ser Pro Lys Asp Asn Thr Val Asp Ala Asn Thr Asn
                1365                1370                1375

Glu Ile Glu Ile Lys Gly Asn Thr Tyr Lys Gly Ala Lys Val Thr Ile
            1380                1385                1390

Asn Asp Glu Ser Phe Val Gln Gln Glu Asn Gly Val Phe Thr Lys Val
        1395                1400                1405

Val Pro Leu Glu Tyr Gly Val Asn Thr Thr Lys Ile His Val Glu Pro
    1410                1415                1420

Ser Gly Asp Lys Asn Asn Glu Leu Thr Lys Asp Ile Thr Ile Thr Val
1425                1430                1435                1440

Ile Arg Glu Glu Pro Val Gln Glu Lys Glu Pro Thr Pro Thr Pro Glu
                1445                1450                1455

Ser Glu Pro Ala Pro Met Pro Glu Pro Gln Pro Thr Pro Thr Pro Glu
            1460                1465                1470

Pro Gln Pro Ser Ala Ile Met Ala Leu
        1475                1480

<210> SEQ ID NO 2
<211> LENGTH: 2863
<212> TYPE: DNA
<213> ORGANISM: Thermoana  ethanolicus

<400> SEQUENCE: 2
ttaagcttgc atcttgattc agattctgta gtaactttt  attacaacta taatacttca      60
agtgttactg attcacaaaa tatacaccaa ttccggaaga aaacttcca agaattgtag     120 gtactataca atcagcaata ggagcaggtg atgattggaa acctgaaaca tcgacagcta     180
taatgagaga ctataagttt aacaatgttt acgaataca  tgcaaatgtt ccaaaaaggt     240
attatgagtt taaagtaact ttagggcccct catgggatat aaattatggc ttaaatggtg     300
aacaaaatgg tccaaatatt cctttgaatg tagcctatga tactaagatt acattttact     360
atgattcggt ttcacataat atatggacag attacaatcc cctctcaca  gggcctgata     420 ataacatata ttatgacgat ttaaaacatg acacccatga cccattcttc cgcttcgctt     480
tcggtgcaat aaaaacaggt gatacagtga ctttgaggat acaggctaaa atcatgacc      540 ttgagtcagc taaaatttct tattgggatg atattaaaaa aacaagaaca gaagtcccga     600
tgtataaaat tggtcaaagt cctgacgggc aatatgaata ctgggaagtg aagttaagct     660
ttgactatcc cacaagaatt tggtattact ttatacttaa agacgggaca aaaactgctt     720
attacggaga taacgatgaa caattaggtg gagtaggtaa agccacagat acggtaaata     780
aagactttga acttactgta tacgataaaa atttagacac ccctgattgg atgaaagggg     840
cagtaatgta tcaaatattc ccagatagat tttacaatgg tgacccttta aatgaccgcc     900
taaaggaata cagtagaggt tttgatcctg ttgaatatca tgacgactgg tatgaccttc     960
ccgacaatcc gaatgataaa gataaacctg gatacaggg  ggatggtata tggaataatg    1020
acttctttgg tggtgatttta caaggtataa atgataaatt ggattatcta aaaaaccttg    1080
gaatatcagt tatttatctc aatccaattt tccaatcacc ttccaatcac cgatatgata    1140
caaccgatta cacaaagata gacgagttat tgggagattt agatacattt aaaacactta    1200
tgaaagaagc ccatgcaaga ggaattaaag taatacttga tggcgtcttc aatcatacaa    1260
```

-continued

```
gtgatgatag tatttatttt gatagatacg ggaagtactt ggataatgaa ttaggtgctt   1320
atcaagcctg gaaacaggga gatcagtcaa aatctccata cggtgactgg tacgaaatta   1380
agcctgacgg tacctatgag ggctggtggg gatttgacag cttaccggta ataaggcaga   1440
taaacggaag tgagtacaat gtaaaaagtt gggcagattt tatcataaat aatcctaatg   1500
caatatctaa gtattggtta aatcctgatg gggataaaga tgcaggtgca gatggctgga   1560
gattggatgt tgcaaatgaa attgctcacg atttctgggt tcattttaga gctgcaatta   1620
atactgtgaa accaaatgcg ccaatgattg cagaactttg gggagatgct tcattagatt   1680
tacttggaga ttcttttaac tctgttatga actatctttt tagaaatgca gttattgatt   1740
ttatactcga taaacagttt gatgatgaaa atgtggttca caatcctata gatgcagcaa   1800
aacttgacca aaggcttatg agcatatatg agagatatcc tcttccagta ttttattcta   1860
ctatgaacct tttaggttct catgacacca tgagaatatt gacagtattt ggatataact   1920
ctgctaatga aaatcaaaat tctcaagagg cgaaagacct tgcagttaag aggcttaaac   1980
ttgccgcaat attgcaaatg ggctatccgg gaatgccttc tatttactat ggtgacgagg   2040
caggacaatc tggtggaaaa gacccagata acaggagaac attctcttgg ggaagagaag   2100
ataaagatct gcaggatttc tttaagaaag tcgtaaacat aaggaatgaa atcaagtttt   2160
taaaaacagg agaccttgaa acactttatg caaatggcga tgtttatgcc tttggaagaa   2220
gaattataaa tggaaaagat gtatttggta attcttatcc tgacagtgta gctattgttg   2280
tgattaataa aggtgaggca aagtcagtac aaatagatac tactaaattt gtaagagatg   2340
gagttgcttt tacagatgcc ttaagtggta agacatacac ggttcgtgat ggacaaattg   2400
ttgtagaagt tgtggcattg gatggggcta tactcatttc agatccagga cagaatttga   2460
cggcacctca gccaataaca gaccttaaag cagtttcagg aaatggtcaa gtagacccttt   2520 cgtggagtgc agtagataga gcagtaagtt ataacattta ccgctctaca gtcaaaggag   2580
ggctatatga aaaaatagct tcaaatgtta cgcaaattac ttatattgat acagatgtta   2640
ccaatggtct aaagtatgtg tattctgtaa cggctgtaga tagtgatgga aatgaaagtg   2700
ctttaagcaa tgagttgagg catatccagc attttctatt ggttgggcag gaaatatgaa   2760
ccaagttgat acccatgtaa taggcgtaaa taatccagtt gaagtttatg ctgaaatttg   2820
ggcagaagga ttaacagata aacctggcca aggggaaaat atg                     2863
```

```
<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
ggggaattcg atctcgattt ttgaggaat                                29
```

```
<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
gggggatccc atagctattt gtacttgct                                29
```

```
<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
gggggatccg ggattaaata gctgggcca                              29

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
cgggattcct taagcttgca tcttga                                 26

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
ccggcggccg cctacatatt ttccccttgg cca                         33

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
tccgagctcc agatcgttca aacattt                                27

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
agcgagctcg atcgatctag taacat                                 26

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
cgccgcggta gctttagcta tagcgat                                27

<210> SEQ ID NO 11
<211> LENGTH: 27
<212> TYPE: DNA
<213> ORGANISM: Artificial Sequence
<220> FEATURE:
<223> OTHER INFORMATION: Primer
```

```
<400> SEQUENCE: 11
tccccgcggg tcctctaagt gaaccgt                                        27

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
cgcatatgtt aagcttgcat cttgattc                                       28

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
ccgctcgagc tacatatttt cccttggcc a                                    31
```

TRANSGENIC SEEDS EXPRESSING AMYLOPULLULANASE AND USES THEREFOR

BACKGROUND

Rice seeds contain abundant starch and have been commonly used in the food and beverage industries. Generally, rice seed contains 6–10% of protein and 70–80% of starch of total seed weight, and the protein and starch can be separated for processing into different products. The traditional process for separating rice protein from starch can be tedious and costly, while the use of chemicals, e.g., sodium hydroxide, acids, and surfactants, is undesirable in food production. As an alternative, an enzymatic process can produce high-maltose syrup and high-protein rice flour from milled rice (Shaw and Sheu, 1992, Biosci. Biotech. Biochem. 56:1071–1073). In this process, the rice flour is first liquefied with thermostable microbial α-amylase at high temperature and the heat-coagulated protein is separated from the soluble starch hydrolysate and recovered as high-protein rice flour. The starch hydrolysate is further treated with microbial β-amylase and debranching enzyme (isoamylase and/or pullulanase) to produce high-maltose syrup. The syrup can be used for food processing and alcohol beverage production. The high-protein rice flour has high nutritional value and is useful for the production of pudding, gruel, instant milk, baby food, etc.

The development of other alternative methods to facilitate utilization of cereal seed starch is desirable.

SUMMARY OF THE INVENTION

The invention is based, in part, on the inventor's surprising discovery that a microbial amylopullulanase (APU), e.g., *Thermoanaerobacter ethanolicus* APU, e.g., a truncated *T. ethanolicus* APU, when expressed under the control of a seed specific promoter in a seed, e.g., a germinated seed, shows a specific activity several-fold higher than when expressed in *E. coli*. Thus, a system has been developed and is described herein, whereby *T. ethanolicus* APU, e.g., a truncated *T. ethanolicus* APU, e.g., a *T. ethanolicus* APU lacking amino acids 1–105 and 1061–1481 of the mature APU (SEQ ID NO:1), is expressed in a seed (e.g., a rice seed), thereby producing a seed with an altered starch or protein content. Such seeds can be used in the production of plant starches or sugars beneficial to numerous industries, including the cereal and beverage production industries.

When a *T. ethanolicus* APU sequence is said to be free of amino acids 1–105 and 1061–1481 of SEQ ID NO:1, it means that the APU sequence does not contain the complete sequence defined by amino acids 1–105 and 1061–1481 of SEQ ID NO:1. Thus, the APU sequence can contain a portion of amino acids 1–105 and 1061–1481 of SEQ ID NO:1 and still be considered free of amino acids 1–105 and 1061–1481 of SEQ ID NO:1. Suitable truncated APU sequences for use in the constructs described herein can even contain all but one, 25, 50, 100, 150, 200, 300, 400, 500, or more amino acids defined by the sequences of 1–105 and 1061–1481 of SEQ ID NO:1 and still be considered free of SEQ ID NO:1.

Accordingly, in one aspect, the present invention features a DNA construct that includes a nucleotide sequence encoding a microbial amylopullulanase or a fragment thereof having pullulanase and α-amylase activities, operably linked to a seed-specific promoter. The microbial amylopullulanase can be *T. ethanolicus* Amylopullulanase, e.g., *T. ethanolicus* 39E Amylopullulanase. In one aspect, a truncated *T. ethanolicus* 39E Amylopullulanase that retains both α-amylase and pullulanase activities is used, e.g., the construct includes a nucleotide sequence encoding a truncated *T. ethanolicus* 39E Amylopullulanase that is free of amino acids 1–105 and 1061–1481 of SEQ ID NO:1. The construct can also include a sequence encoding a signal peptide, e.g., a glutelin signal peptide, upstream of the Amylopullulanase coding sequence. In addition, the construct can include a 3' gene terminator sequence, e.g., a nopaline synthase gene terminator sequence. The seed specific promoter of the construct can be any plant promoter that is expressed in seeds, preferably in germinating or developing seeds. Exemplary seed specific promoters include a glutelin promoter, e.g., the GluB promoter and an α-Amy promoter, e.g., α-Amy3 or αAmy8 promoters.

In another aspect, the invention features a genetically engineered seed, e.g., a rice, corn, wheat, or barley seed, that includes a DNA construct having a nucleotide sequence encoding a microbial amylopullulanase enzyme or a fragment thereof having pullulanase and α-amylase activities, operably linked to a seed-specific promoter, e.g., a DNA construct described hereinabove. Such seeds can have a modified starch structure or content, including reduced amylose content or altered total starch composition compared to naturally occurring seeds. Such seeds can thus be the source of sugars and high protein seed products.

In yet another aspect, the invention features a method of producing a starch having a modified structure. The method includes the steps of: (a) transforming a plant cell with a DNA construct that includes a nucleotide sequence encoding a microbial amylopullulanase or a fragment thereof having pullulanase and α-amylase activities, operably linked to a seed-specific promoter, e.g., a DNA construct described hereinabove; (b) generating a whole plant from the transformed plant cell; (c) optionally multiplying the whole plant; (d) harvesting seeds from the whole plant or multiplied whole plants; and (e) extracting the starch from the seeds. The seed can be a rice, corn, wheat, or barley seed. In a preferred embodiment, the seed is a rice seed.

In another aspect, the invention features a method of producing a sugar. The method includes: (a) transforming a plant cell with a DNA construct comprising a seed specific promoter operatively linked to a nucleotide sequence encoding a microbial amylopullulanase or a fragment thereof having pullulanase and α-amylase activities, e.g., a DNA construct described herein; (b) generating a whole plant from the transformed plant cell; (c) optionally multiplying the whole plant; (d) harvesting seeds from the whole plant or multiplied whole plants; and (e) treating the seeds, or starch extracted from the seeds, under conditions sufficient to convert the starch in the seeds or the starch extracted from the seeds, to sugar. In one embodiment, the seed is a rice seed. An exemplary manner of treating the seeds, or starch extracted from the seeds, includes heating the seeds, or starch extracted from the seeds, until the starch turns to sugar. For example, the seeds or starch can be heated to between about 60 to 95° C., e.g., at least about 60° C., 70° C., 75° C., 80° C., 85° C., 90° C., 95° C.

In yet another aspect, the invention features a method of making a polypeptide. The method includes: providing a nucleic acid construct that includes a glutelin promoter, e.g., a GluB promoter, operatively linked to a nucleic acid sequence encoding a heterologous polypeptide, e.g., an enzyme or functional fragment thereof, e.g., a bacterial enzyme or functional fragment thereof; introducing the nucleic acid construct into a cell, e.g. a plant cell, e.g., a rice cell; and allowing the cell to express the polypeptide encoded by the coding sequence. The sequence encoding the heterologous polypeptide optionally includes a signal sequence, e.g., a glutelin signal sequence. The cell can be a tissue culture cell. In one embodiment, the cell is a seed cell and the polypeptide is expressed in the endosperm of a germinating seed. In another embodiment, the cell is a seed cell and the polypeptide is expressed in the embryo of a developing seed. In another embodiment, the cell is a tissue culture cell and the polypeptide is secreted into the culture medium of the cell.

A "DNA construct" is defined herein as a DNA molecule that has been modified to contain segments of DNA that are combined and juxtaposed in a manner that would not otherwise exist in nature. The term encompasses plasmid and viral constructs.

DETAILED DESCRIPTION OF THE INVENTION

Figure 1:
FIG. 1 is a depiction of expression cassettes for rice transformation: (A) pGApu contains the GluB-1 promoter fused upstream of the Apu cDNA and Nos 3' downstream of the Apu cDNA; (B) pGpApu contains the GluB-1 promoter and signal peptide sequence fused upstream of the Apu cDNA and Nos 3' downstream of the Apu cDNA; (C) pA3Apu contains the αAmy3 promoter and signal peptide sequence fused upstream of the Apu cDNA and αAmy3 3' downstream of the Apu cDNA; (D) pA8Apu contains the αAmy8 promoter and signal peptide sequence fused upstream of the Apu cDNA and αAmy8 3' downstream of the Apu cDNA.
Figure 1:
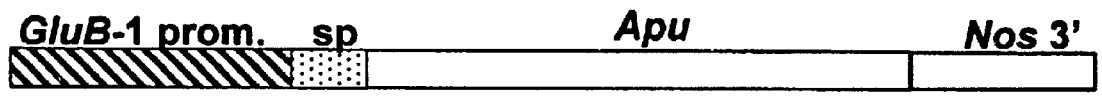
Figure 1:
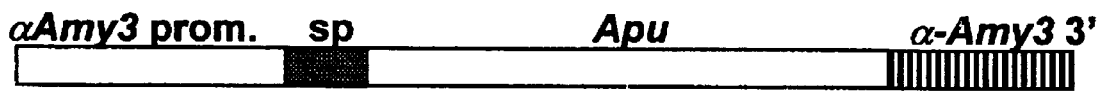
Figure 1:

Constructs, seeds and related methods are described herein that use a transgenic approach in the production of cereal seed starch. Cereal seeds such as rice seeds, e.g., developing or germinated rice seeds, can be engineered for expression of microbial APU under control of seed-specific promoters. For example, T. ethanolicus APU is expressed in developing seeds under the control of the glutelin gene (GluB-1) promoter, and in germinated seeds under the control of two α-amylase gene promoters (αAmy3 and αAmy8). A 2.9-kb DNA fragment of T. ethanolicus 39E Apu gene encoding a truncated form of APU can be used in the constructs described herein. The truncated APU maintains both α-amylase and pullulanase activities.

Amylopullulanase (APU) from Thermoanaerobacter ethanolicus 39E, harboring both pullulanase and a-amylase activities, is capable of hydrolyzing both α-1,4 and α-1,6 bonds of polysaccharides and is heat stable with a catalytic optimum of 90° C. (Saha et al. (1988) Biochem. J. 252:343–348). The results described herein show that, unexpectedly, under the control of GluB-1 promoter, truncated APU was expressed in embryo of developing seeds and in cultured rice suspension cells provided with sucrose. Under the control of αAmy3 or αAmy8 promoter, APU was also expressed in embryo and endosperm of developing seeds. The specific activity of truncated APU expressed in germinated seeds was several-fold higher than that expressed in E. coli. Amylose content was generally reduced, and the reduction correlates inversely with the APU level in transgenic rice seeds. Starch in rice seeds expressing truncated APU was completely converted to sugars, e.g., within 8 hr when heated at 70° C. or within 4 h when heated at 85° C. The data described herein demonstrate that one can obtain APU-containing rice seeds by expressing a microbial enzyme under the control of seed-specific promoters in transgenic seeds, e.g., rice seeds. The data described herein also demonstrate an approach to alter amylose content and rapidly liquefy starch in rice seeds, which offers to starch processing and beverage industries the opportunity of producing inexpensive products from plant starch. The use of the transgenic seeds, e.g., rice seeds, containing the dual active APU can facilitate the simultaneous liquefication and saccharification of starch at high temperature without the need to add exogenous α-amylase and pullulanase.

The amino acid sequence of T. ethanolicus APU (Genbank Accession No. A47341) is shown below.

```
MFKRRTLGFL  LSFLLIYTAV  FGSMPVQFAK  AETDTAPAIA  NVVGDFQSKI  GDSDWNINSD    (SEQ ID NO:1)

KTVMTYKGNG  FYEFTTPVAL  PAGDYEYKVA  LNHSWEGGGV  PSQGNLSLHL  DSDSVVTFYY

NYNTSSVTDS  TKYTPIPEEK  LPRIVGTIQS  ATGAGDDWKP  ETSTAIMRDY  KFNNVYEYTA

NVPKRYYEFK  VTLGPSWDIN  YGLNGEQNGP  NIPLNVAYDT  KITFYYDSVS  HNTWTDYNPP

LTGPDNNIYY  DDLKHDTHDP  FFRFAFGAIK  TGDTVTLRIQ  AKNHDLESAK  ISYWDDTKKT

RTEVPMYKIG  QSPDGQYEYW  EVKLSFDYPT  RIWYYFILKD  GTKTAYYGDN  DEQLGGVGKA

TDTVNKDFEL  TVYDKNLDTP  DWMKGAVMYQ  IFPDRFYNGD  PLNDRLKEYS  RGFDPVEYHD

DWYDLPDNPN  DKDKPGYTGD  GTWNNDFFGG  DLQGINDKLD  YLKNLGISVI  YLNPIFQSPS

NHRYDTTDYT  KIDELLGDLD  TFKTLMKEAH  ARGIKVILDG  VFNHTSDDSI  YFDRYGKYLD

NELGAYQAWK  QGDQSKSPYG  DWYEIKPDGT  YEGWWGFDSL  PVTRQTNGSE  YNVKSWADFI

INNPNAISKY  WLNPDGDKDA  GADGWRLDVA  NEIAHDFWVH  FRAAINTVKP  NAPMIAELWG

DASLDLLGDS  FNSVMNYLFR  NAVIDFILDK  QFDDGNVVHN  PIDAAKLDQR  LMSIYERYPL

PVFYSTMNLL  GSHDTMRILT  VFGYNSANEN  QNSQEAKDLA  VKRLKLAAIL  QMGYPGMPSI

YYGDEAGQSG  GKDPDNRRTF  SWGREDKDLQ  DFFKKVVNIR  NENQVLKTGD  LETLYANGDV

YAFGRRIING  KDVFGNSYPD  SVAIVVINKG  EAKSVQIDTT  KFVRDGVAFT  DALSGKTYTV
```

RDGQIVVEVV ALDGATLISD PGQNLTAPQP ITDLKAVSGN GQVDLSWSAV DRAVSYNIYR

STVKGGLYEK IASNVTQTTY IDTDVTNGLK YVYSVTAVDS DGNESALSNE VEAYPAFSIG

WAGNMNQVDT HVIGVNNPVE VYAETWAEGL TDKPGQGENM TAQLGYRYTG DGGQDATRNK

VEGVEINKDW TWVDARYVGD SGNNDKYMAK FVPDMVGTWE YIMRFSSNQG QDWTYTKGPD

GKTDEAKQFI VVPSNDVEPP TALGLQQPGI ESSRVTLNWS LSTDNVAIYG YEIYKSLSET

GPFVKIATVA DTVYNYVDTD VVNGKVYYYK VVAVDTSFNR TASNTVKATP DIIPIKVIFN

VTVPDYTPDD GANIAGNFHD AFWNPSAHQM TKTGPNTYSI TLTLNEGTQL EYKYARGSWD

KVEKGEYGEE IANRKITVVN QGSNTMVVND TVQRWRDLPI YIYSPKDNTT VDANTNEIEI

KGNTYKGAKV TINDESFVQQ ENGVFTKVVP LEYGVNTTKI HVEPSGDKNN ELTKDITITV

IREEPVQEKE PTPTPESEPA PMPEPQPTPT PEPQPSATMA L

Shown below is the nucleotide sequence of the approximately 2.9-kb DNA fragment of Apu gene that encodes amino acids 106 to 1060 of the mature APU of *T. ethanolicus*.

(SEQ ID NO:2)

```
TTAAGCTTGCATCTTGATTCAGATTCTGTAGTAACTTTTTATTACAACTATAATACTTCAAGTGTTACTGA
TTCACAAAATATACACCAATTCCGGAAGAAAAACTTCCAAGAATTGTAGGTACTATACAATCAGCAATAGG
AGCAGGTGATGATTGGAAACCTGAAACATCGACAGCTATAATGAGAGACTATAAGTTTAACAATGTTTACG
AATACACTGCAAATGTTCCAAAAAGGTATTATGAGTTTAAAGTAACTTTAGGGCCCTCATGGGATATAAAT
TATGGCTTAAATGGTGAACAAAATGGTCCAAATATTCCTTTGAATGTAGCCTATGATACTAAGATTACATT
TTACTATGATTCGGTTTCACATAATATATGGACAGATTACAATCCACCTCTCACAGGGCCTGATAATAACA
TATATTATGACGATTTAAAACATGACACCCATGACCCATTCTTCCGCTTCGCTTTCGGTGCAATAAAAACA
GGTGATACAGTGACTTTGAGGATACAGGCTAAAAATCATGACCTTGAGTCAGCTAATATTTCTTATTGGGA
TGATATTAAAAAACAAGAACAGAAGTCCCGATGTATAAAAATTGGTCAAAGTCCTGACGGGCAATATGAAT
ACTGGGAAGTGAAGTTAAGCTTTGACTATCCCACAAGAATTTGGTATTACTTTATACTTAAAGACGGGACA
AAAACTGCTTATTACGGAGATAACGATGAACAATTAGGTGGAGTAGGTAAAGCCACAGATACGGTAAATAA
AGACTTTGAACTTACTGTATACGATAAAAATTTAGACACCCCTGATTGGATGAAAGGGGCAGTAATGTATC
AAATATTCCCAGATAGATTTTACAATGGTGACCCTTTAAATGACCGCCTAAAGGAATACAGTAGAGGTTTT
GATCCTGTTGAATATCATGACGACTGGTATGACCTTCCCGACAATCCGAATGATAAAGATAAACCTGGATA
TACAGGGGATGGTATATGGAATAATGACTTCTTTGGTGGTGATTTACAAGGTATAAATGATAAATTGGATT
ATCTAAAAAACCTTGCAATATCAGTTATTTATCTCAATCCAATTTTCCAATCACCTTCCAATCACCGATAT
GATACAACCGATTACACAAAGATAGACGAGTTATTGGGAGATTTAGATACATTTAAAACACTTATGAAAGA
AGCCCATGCAAGAGGAATTAAAGTAATACTTGATGGCGTCTTCAATCATACAAGTGATGATAGTATTTATT
TTGATAGATACGGGAAGTACTTGGATAATGAATTAGGTGCTTATCAAGCCTGGAAACAGGGAGATCAGTCA
AAATCTCCATACGGTGACTGGTACGAAATTAAGCCTGACGGTACCTATGAGGGCTGGTGGGGATTTGACAG
CTTACCGGTAAIAAGGCAGATAAACGGAAGTGAGTACAATGTAAAAAGTTGGGCAGATTTTATCATAAATA
ATCCTAATGCAATATCTAAGTATTGGTTAAATCCTGATGGGGATAAAGATGCAGGTGCAGATGGCTGGAGA
TTGGATGTTGCAAATGAAATTGCTCACGATTTCTGGGTTCATTTTAGAGCTGCAATTAATACTGTGAAACC
AAATGCGCCAATGATTGCAGAACTTTGGGGAGATGCTTCATTAGATTTACTTGGAGATTCTTTTAACTCTG
TTATGAACTATCTTTTTAGAAATGCAGTTATTGATTTTATACTCGATAAACAGTTTGATGATGGAAATGTG
GTTCACAATCCTATAGATGCAGCAAAACTTGACCAAAGGCTTATGAGCATATATGAGAGATATCCTCTTCC
```

-continued

```
AGTATTTTATTCTACTATGAACCTTTTAGGTTCTCATGACACCATGAGAATATTGACAGTATTTGGATATA

ACTCTGCTAATGAAAATCAAAATTCTCAAGAGGCGAAAGACCTTGCAGTTAAGAGGCTTAAACTTGCCGCA

ATATTGCAAATGGGCTATCCGGGAATGCCTTCTATTTACTATGGTGACGAGGCAGGACAATCTGGTGGAAA

AGACCCAGATAACAGGAGAACATTCTCTTGGGGAAGAGAAGATAAAGATCTGCAGGATTTCTTTAAGAAAG

TCGTAAACATAAGGAATGAPAATCAAGTTTTAAAAACAGGAGACCTTGAAACACTTTATGCAAATGGCGAT

GTTTATGCCTTTGGAAGAAGAATTATAAATGGAAAAGATGTATTTGGTAATTCTTATCCTGACAGTGTAGC

TATTGTTGTCATTAATAAAGGTGAGGCAAAGTCAGTACAAATAGATACTACTAAATTTGTAAGAGATGGAG

TTGCTTTTACAGATCCCTTAAGTGGTAAGACATACACGGTTCGTGATGGACAAATTGTTGTAGAAGTTGTG

GCATTGGATCGGGCTATACTCATTTCAGATCCAGCACAGAATTTGACGGCACCTCAGCCAATAACACACCT

TAAAGCAGTTTCAGGAAATGGTCAAGTAGACCTTTCGTGGAGTGCAGTAGATAGAGCAGTAAGTTATAACA

TTTACCGCTCTACAGTCAAAGGAGGGCTATATGAAAAAATAGCTTCAAATGTTACGCAAATTACTTATATT

GATACAGATGTTACCAATGGTCTAAAGTATGTGTATTCTGTAACGGCTGTAGATAGTGATGGAAATGAAAG

TGCTTTAAGCAATGAGTTGAGGCATATCCAGCATTTTCTATTGGTTGGGCAGGAAATATGAACCAAGTTGA

TACCCATGTAATAGGCGTAAATAATCCAGTTGAAGTTTATGCTGAAATTTGGGCAGAAGGATTAACAGATA

AACCTGGCCAAGGGGAAAATATG
```

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Example 1

Construction of Chimeric Genes, Transformation and Selection of Transformed Rice Cells A 2.9-kb DNA fragment of Apu gene that encodes amino acids 106 to 1060 of the mature APU of T. ethanolicus was isolated (shown as SEQ ID NO:2). This truncated APU expressed in E. coli maintains both α-amylase and pullulanase activities. A DNA fragment containing the 1351-bp rice GluB-1 promoter only or the promoter plus a 75-bp sequence encoding a putative 25-amino acid signal peptide of GluB was individually placed upstream of the coding region of Apu to make translational fusion constructs, and the nopaline synthase gene terminator (Nos 3') was placed downstream of the Apu coding region. The putative 25-amino acid signal peptide cleavage site was predicted based on a statistical method (von Heijne (1985) J. Mol. Biol. 184:99–105). The signal peptide sequence can be used to target APU to different cellular compartments, e.g., cytoplasm and endospermic reticulum. The chimeric DNAs were then inserted into the binary vector pSMY1H (Ho et al. (2000) Plant Physiol 122:57–66) to generate pGApu and pGpApu (FIG. 1A and FIG. 1B). The 1.1- and 1.2-kb promoter and signal peptide sequences of αAmy3 and αAmy8, respectively, were placed upstream of the coding region of Apu to make a translation fusion, and the 3' untranslated regions of αAmy3 and αAmy8 were placed downstream of the αAmy3-Apu and αAmy8-Apu chimeric genes, respectively. The chimeric DNAs were then inserted into pSMY1H to generate pA3Apu and pA8Apu (FIG. 1C and FIG. 1D). These plasmids were individually delivered into the rice genome via Agrobacterium-mediated transformation. The putative transformed rice calli were selected on medium containing hygromycin. Identification of the transformed rice cells was then confirmed with standard genomic DNA Southern blot analysis.

Example 2

APU Expression Under Control of the GluB and α-Amy Promoters is Sugar-Regulated in Transformed Rice Suspension Cells The transformed rice calli were cultured in liquid MS medium to generate suspension cell culture. The culture media of cells expressing APU with signal peptides were collected and analyzed for APU accumulation. Levels of APU were significantly higher in media of transformed suspension cells than those in media of non-transformed cells. The levels of APU varied from line to line, indicating a position effect on transgene expression. Presence of APU in the culture media indicates that the putative signal sequence of GluB-1, when used, is capable of directing translocation of APU through the secretary pathway. The αAmy3 and αAmy8 promoters directed higher levels of APU expression in the absence of sucrose than in the presence of sucrose, which was expected as activity of αAmy3 and αAmy8 promoters is up-regulated by sucrose starvation (Chan et al. (1994) J. Biol. Chem. 269:17635–17641; Lu et al. (1998) J. Biol. Chem. 273:10120–10131). Interestingly, the GluB-1 promoter directed higher level of APU expression in rice suspension cells in the presence of sucrose than in the absence of sucrose, which suggests that activity of the GluB-1 promoter is up-regulated by sucrose in cultured rice suspension cells.

The 1.3-kb long GluB-1 promoter has been shown to direct endosperm-specific expression of a reporter gene in transgenic rice (Wu et al. (1998) Plant Cell Physiol. 39:885–889). As described herein, the same length of GluB-1 promoter is capable of directing APU expression in cultured rice suspension cells and embryo, in addition to endosperm, of developing rice seeds. In cultured rice suspension cells, the GluB-1 promoter is up-regulated by sucrose and its signal peptide sequence directs secretion of APU into the culture medium. Promoter active in cultured cells and/or up-regulated by sugars seems to be a common phenomenon for storage protein genes. For example, a promoter of another rice seed storage protein, prolamin, has been shown to be active in cultured cells. Promoters of other storage proteins, e.g., sporamin and β-amylase of sweet potato and patatin and proteinase inhibitor II of potato, have been shown to be up-regulated by sugars in leaf, stem, or tuber (Koch (1996) Annu. Rev. Plant Physiol. Plant Mol. Biol. 47:509–540). Expression of storage protein genes is most active in developing storage organs, and the developing storage organs are sink tissues for adsorption of sugars produced in source tissues, e.g., leaf. Consequently, it is reasonable for storage protein genes to be up-regulated by sugars.

It is well recognized that in cereals, a-amylase genes are mainly expressed in germinating or germinated seeds (Yu (1999) Molecular Biology of Rice. K. Shimamoto (ed.), Chapter 9. Springer-Verlag, Tokyo. pp. 161–178). In germinated rice seeds, mRNA of several α-amylase genes could be detected in embryo and endosperm (Karrer et al. (1991) Plant Mol. Biol. 16:797–805; Yu et al. (1996) Plant Mol Biol 30:1277–1289). Expression of αAmy3 and αAmy8 is transient in embryo and fluctuate in endosperm of rice seeds during a 9-day germination period (Yu et al., 1996, supra). In transgenic rice seeds, the αAmy7 promoter has been shown to direct reporter gene expression in both embryo and endosperm during and post germination. Activity of the αAmy7 promoter is not detected prior to germination, peaked 4 and 6 days and then decreased to low level 8 days after germination (Itoh et al. (1995) Plant Physiol. 107:25–31). In the developing seeds, the concentration of α-amylase in embryo was 20 and 60 times higher than that in endosperm and pericarp, respectively (Thévenot et al. (1992) J. Plant Physiol. 140:61–65). In the present study, it has been demonstrated that APU expressed under control of the αAmy3 and αAmy8 promoters accumulate in both embryo and endosperm of mature transgenic rice seeds and in germinated transgenic rice seeds. All these studies indicate that activity of α-amylase gene promoters is subject to repeated activation and repression during seed development and germination. Expression of a-amylase genes in germinating rice seeds can be induced by GA and suppressed by ABA or sugars (Karrer et al. (1992) Plant J. 2:517–523.; Itoh et al., 1995, supra; Yu et al., 1996, supra).

Example 3

APU Expressed Under Control of the GluB and αAmy Promoters Accumulates in Germinated Transgenic Rice Seeds Transformed rice calli were regenerated, self-fertilized for two generations, and T2 homozygous seeds were obtained. Homozygosity of transgenic seeds was determined by germination of 25 transgenic seeds in water containing 50 μg/ml hygromycin for 7 days and calculation of the ratio between numbers of growing and non-growing seeds. Homozygous seeds will all germinate in the presence of hygromycin. T2 homozygous seeds of transgenic rice lines carrying different constructs were germinated and grown for 5 days. The entire germinated seeds were extracted and APU level was determined. APU expressed under the control of GluB-1, αAmy3 and αAmy8 promoters accumulated in germinated seeds, with levels significantly higher than that in non-transformant. Although the levels of APU varied from line to line, the αAmy8 promoter generally confers higher levels of APU expression than the αAmy3 and GluB-1 promoters in germinated transgenic rice seeds.

Example 4

APU Expressed Under Control of the GluB and αAmy Promoters Accumulates in Embryo and Endosperm of Mature Transgenic Rice Seeds Five transgenic lines carrying different constructs and accumulated high levels of APU in germinated transgenic rice seeds were selected for further analysis of APU accumulation in mature seeds. The embryos and endosperms of T2 homozygous seeds were separately collected and APU levels were determined. APU expressed under control of the GluB-1, αAmy3 and αAmy8 promoters accumulated in both embryos and endosperms of mature seeds, with levels significantly higher than those in non-transformed seeds. The GluB-1 promoter appears to confer higher levels of APU expression than the αAmy3 and αAmy8 promoters in the two tissues.

Example 5

The GluB Promoter Directs APU Expression in Embryo and Endosperm of Developing Transgenic Rice Seeds The GluB-1 promoter has been reported to direct endosperm-specific expression of a reporter gene in developing rice seeds (Wu et al. (1998) Plant J. 14:673–683; Wu et al. (1998) Plant Cell Physiol. 39:885–889). In the present study, APU expressed under control of the GluB-1 promoter was detected in germinated seed and embryo, in addition to endosperm, of mature seeds. APU present in the embryo of mature seeds must accumulate during seed development. Consequently, activity of GluB-1 promoter in germinated seed and embryo of developing seeds was further investigated. Mature transgenic rice seeds carrying the GluB-Apu construct were germinated for 1, 3, and 5 days. Developing transgenic rice seeds carrying the GluB-Apu construct were also collected at 5, 10, 15, and 25 days after pollination (DAP). In situ hybridization technique was applied for detection of the Apu mRNA present in tissues. The Apu mRNA was detected neither in endosperm nor in embryo of germinated rice seeds. However, the Apu mRNA was detected in embryo and endosperm of rice seeds of different developing stages. The Apu mRNA accumulated throughout all the tissues of endosperm and embryo of transgenic rice seeds of 10 and 15 DAP. In embryo, accumulation of the Apu mRNA was significantly higher in shoot apex, primary leaf, and coleoptile than in scutellum. Immunohistochemistry technique using the anti-APU antibodies was also applied for detection of APU present in tissues. Similarly, APU accumulated throughout all the tissues of endosperm and embryo of transgenic rice seeds of 15 DAP. In embryo, accumulation of APU was significantly higher in coleoptile than in other tissues. This example demonstrate that the GluB-1 promoter is not active in embryo and endosperm of germinated rice seeds but is active in embryo and endosperm of developing rice seeds.

Example 6

APU Expressed in Germinated Transgenic Rice Seeds has High Specific Activity To determine whether APU expressed in germinated transgenic rice seeds is active, T2 homozygous seeds of transgenic rice carrying different constructs were germinated and grown for 5 days. Cell extract of the entire germinated seeds was prepared and APU level was determined. Cell extract was also incubated at 90° C. for 30 min and APU activity per equal amount of APU present in cell extract was determined. The *E. coli*-expressed APU was used as a control. APU expressed in all of the germinated transgenic seeds was active and unexpectedly had a specific activity 3 to 4-fold of that expressed in *E. coli*.

While the authors do not wish to be bound by theory, there could be several reasons for this unexpected result. First, there are many endogenous starch hydrolyzing enzymes present in germinated rice endosperm (Kubo et al. (1999) Plant Phystiol. 121:399–409). These hydrolytic enzymes may have a synergistic effect on APU activity in germinated seeds, as APU activity was assayed in the presence of the cell extract of entire germinated seeds. Second, there are three potential glycosylation sites in the APU polypeptide. Post-translational modification of APU may have increased the specific activity of this enzyme in germinated seeds. Third, APU expressed in germinated rice seeds was folded into a conformation that gives better activity. Fourth, APU expressed in germinated rice seeds was supposed to have a molecular weight of 110 kD. It was found that large proportion of APU present in germinated rice seeds was truncated to a molecular weight of 40 kD. The truncated APU may have a higher specific activity than the 110 kD APU.

Example 7

Amylose Content is Altered in Transgenic Rice Seeds Expressing APU

The mature seeds of the wild type rice (TNG67) used in the present study generally contain a narrow opaque white region at ventral side of endosperm. However, it was found that the majority of transgenic rice seeds expressing APU contain a much larger opaque white region extended from the ventral side toward the center of endosperm. To determine whether the enlargement of opaque white region correlates with amylose content of endosperm, the amylose content in transgenic rice seeds expressing APU was analyzed. Although varied from line to line, the amylose content was lower in randomly selected transgenic rice lines expressing APU than that in the non-transformed seeds. The amylose content in transgenic rice seeds expressing firefly luciferase (Luc) was similar as those in the non-transformed seeds.

To further determine whether alteration in amylose content is a general phenomenon for rice seeds expressing APU, amylose contents in seeds of 79 transgenic rice lines expressing APU under the control of GluB and αAmy promoters were analyzed. Among these transgenic lines, 9 lines (11%) have higher, 6 lines (8%) have similar, and 64 lines (81%) have reduced amounts of amylose as compared with the non-transformed seeds. Amylose contents of the wild type rice is approximately 19% of total seed weight, while amylose contents of majority transgenic seeds expressing APU range from 11 to 19% of total seed weight. These results indicate that amylose content in rice seeds expressing APU is generally reduced.

Starch is composed of two different glucan chains, amylose and amylopectin. Amylose essentially is a linear polymer of glucosyl residues linked via α-1,4 glucosidic linkages, whereas amylopectin exists as a branched α-1,4; α-1,6 D-glucan polymer. Synthesis of amylose is catalysed by granule-bound starch synthase (GBSS) by addition of one molecule of glucose at a time to the linear α-1,4-glucosyl chain, whereas starch branching enzyme and soluble starch synthase introduce α-1,6 linkages between linear chains to form amylopectin (Preiss (1991) Biology and molecular biology of starch synthesis and its regulation. In: Oxford Surveys of Plant Cellular and Molecular Biology. Vol. 7., ed. Miflin, 59–114, Oxford University Press, Oxford, UK). Reduction in amylose content by expression of antisense GBSS gene have been demonstrated in transgenic potato (Visser et al. (1991) Mol. Gen. Genet. 225:289–296; Salehuzzaman et al. (1993) Plant Mol. Biol. 23:947–962; Kuipers et al. (1994) Plant Cell 6:43–52; Kuipers et al. (1995) Mol. Gen. Genet. 246:745–755) and rice (Shimada et al. (1993) Theor. Appl. Genet. 86:665–672; Terada et al. (2000) Plant Cell Physiol. 41:881–888).

APU is capable of hydrolyzing both α-1,4 and α-1,6 bonds of polysaccharide at high temperature (90° C.). It is intriguing to observe a decrease in amylose content in transgenic rice seeds expressing APU. While not wishing to be bound by theory, one explanation for this phenomenon is that APU exhibits different activity at field temperature (20–30° C.), leading to change in starch biosynthesis during seed development. Our recent study has shown that transgenic rice seeds expressing APU have normal or even slightly higher starch content compared with the non-transformed seeds. Since the amylose content is reduced, there could be an increase in amylopectin and/or phytoglycogen content in these transgenic seeds. If this is the case, it would suggest that APU may possess an undiscovered activity, e.g., starch branching activity, at different temperature. Although the effect on seed starch biosynthesis conferred by APU at field temperature is significant, yield of the transgenic rice appears to be normal.

Example 8

The APU Levels are Inversely Correlated with the Amylose Contents in Transgenic Rice Seeds To determine whether alteration in amylose content correlates with expression level of APU in transgenic rice seeds, transgenic rice lines with different amylose content in seeds were selected for determination of APU levels. The non-transformed seeds had low APU level but high amylose content. However, the transgenic seeds have higher APU levels and lower amylose contents than the non-transformed seeds. Additonally, in the four transgenic rice lines carrying different construct, the higher in APU levels, the lower in amylose content is observed.

These results show that the amylose content correlates inversely with APU level in rice seeds. Consequently, rice seeds contain different amounts of amylose can be obtained by selection of transgenic lines expressing different levels of APU. The modified starch would have altered physico-chemical property and may offer to starch processing industries new applications.

Example 9

Starch in Transgenic Rice Seeds Expressing APU is Completely Converted to Sugars Under Heat Treatment Seeds of a transgenic line produced as described herein was ground to rice flour, suspended in buffer, and incubated at 70° C. or 85° C. for various lengths of time. Prior to heat treatment, level of starch was 68% of total seed weight. Starch was hydrolyzed and concentration of soluble sugar increased rapidly after heating at 70° C. for 8 h or 85° C. for 4 h. Starch disappeared completely and soluble sugars increase to a constant level (70%). This result indicates that starch in rice seeds expressing APU can be completely converted to sugars under appropriate condition. This example thus indicates the feasibility of replacing starch degradation using microbial enzymes by a system where enzymes are produced directly in the starch-containing tissue. Such a manipulation would greatly facilitate production of syrup and high protein flour from the seed starch.

Example 10

Other Methods and Materials

Plant Material

An exemplary rice variety used in the methods and compositions described herein is Oryza sativa L. cv. Tainung 67. Immature seeds are dehulled, sterilized with 2.4% NaOCl for 1 h, washed extensively with sterile water, and placed on N6D agar medium (Toki (1997) Plant Mol Biol Rep 15:16–21) for callus induction. After one month, callus derived from scutella are subcultured in fresh N6D medium for transformation, or to a liquid MS medium containing 3% sucrose and 10 mM 2,4-D to establish a suspension cell culture as previously described (Yu et al. (1991) J Biol Chem 266:21131–21137).

Preparation of Genomic DNA

Rice seeds are germinated and grown in the dark for, e.g., 1 week. *T. ethanolicus* 39E (ATCC53033) was obtained from the American Type Culture Collection. The bacterial and rice genomic DNA was purified from according to the method of Sheu et al. (1996, J Biol Chem 271:26998–27004).

PCR

The 1351-bp glutelin gene promoter region was PCR-amplified using rice genomic DNA as template and B1–5 (5'-GGGGAATTCGATCTCGATTTTTGAGGAAT-3' (SEQ ID NO:3), EcoRI site underlined) as forward primer and B1–3 (5'-GGGGGATCCCATAGCTATTTGTACTTGCT-3' (SEQ ID NO:4), BamHI site underlined) as reverse primer. The glutelin gene promoter plus 75-bp putative signal peptide sequence was PCR-amplified using rice genomic DNA as template and B1–5 as forward primer and B1-sp (5'GGGGGATCCGGGATTAAATAGCTGGGCCA-3' (SEQ ID NO:5), BamHI site underlined) as reverse primer. The truncated Apu encoding amino acid 106 to 1060 was PCR-amplified using genomic DNA of *T. ethanolicus* 39E as template and oligonucleotides 5'-CGGGATT-CCTTAAGCTTGCATCTTGA-3' (SEQ ID NO:6) (BamHI site underlined) as forward primer and 5'-CCGGCGGCCGCCTACATATTTTCCCCTTGGCCA-3' (SEQ ID NO:7) (NotI site underlined) as reverse primer.

Plasmid Construction

The PCR-amplified GluB-1 promoter and GluB-1 promoter-signal peptide sequence were digested with EcoRI and BamHI and subcloned into the same sites in pBluescript (Strategene) to generate pBS-G and pBS-Gp. The truncated Apu was digested with BamHI and NotI and fused downstream of the GluB-1 promoter and GluB-1 promoter-signal peptide sequence in pBS-G and pBS-Gp, respectively, to make translational fusion and to generate pBS-G-Ap and pBS-Gp-Apu. The nopaline synthase gene germinator (Nos 3') was PCR-amplified using pBI221 (Clontech) as DNA templete and oligonucleotide 5'-TCCGAGCTCC-AGATCGTTCAAACATTT-3' (SEQ ID NO:8) (SacI site underlined) as forward primer and oligonucleotide 5'-AGCGAGCTCGATCGATCTAGTAACAT-3' (SEQ ID NO:9) (Sad underlined) site as reverse primer. The Nos 3'UTR was digested with SacI and fused downstream of Apu in pBS-G-Apu and pBS-Gp-Apu to generate pBS-G-Apu-Nos and pBS-Gp-apu-Nos.

The 1.2 kb promoter and signal peptide sequence of αAmy8 was excised with SalI and HindIII from pAG8 (Chan et al., 1993, supra) and subcloned into pBluescript to generate pBS/8sp. The aAmy8 3'UTRs was PCR-amplified using RAMYG6a as DNA template and oligonucleotide 5'-CGCCGCGGTAGCTTTAGCTATAGCGAT-3' (SEQ ID NO.:10) (SacII site underlined) as forward primer and oligonucleotide 5'-TCCCCGCGGGTCCTCTAAGTGAACCGT-3' (SEQ ID NO:11) (SacII underlined) site as reverse primer. Plasmid RAMYG6a contains the 3' half portion of coding sequence and 3' flanking region of αAmy8 genomic DNA and was generated by screening of a rice genomic DNA library (Clontech) using αAmy8-C as a probe (Yu et al. (1992) Gene 122:247–253). The αAmy8 3'UTRs was subcloned into the SacII sites in pBS/8sp to generate pBS/8sp8U. The truncated apu was cut with BamHI and NotI and subcloned into the same sites in pBS-8sp8U to generate pBS-αAmy8-sp-Apu-8U.

The 1.1-kb promoter and signal peptide sequence of αAmy3 was excised with SalI and HindIII from p3G-132II (Lu et al., 1998, supra) and subcloned into pBluescript to generate pBS-3sp. The aAmy3 3'UTR was excised with HindIII and SacI from pMTC37 (Chan and Yu (1998) Plant J 15:685–696) and subcloned into the same sites in pBS-3sp to generate pBS-3sp3U. The truncated Apu was digested with BamHI and NotI and subcloned into the same sites in pBS-3sp3U to generate pBS-αAmy3-sp-Apu-3U.

The correct in-frame fusion of the GluB, αAmy3, and αAmy8 signal peptide sequences with the Apu coding region, and the junction regions which link the Apu coding region with the αAmy3, αAmy8 or Nos 3'UTRs were all verified by DNA sequencing. The GluB-Apu-Nos, GluB-sp-Apu-Nos, αAmy3-sp-Apu-αAmy3 3'UTR and αAmy8-sp-Apu-αAmy8 3'UTR chimeric genes were excised from pBS-G-Apu-Nos, pBS-Gp-Apu-Nos, pBS-αAmy3-sp-Apu-3U, and pBS-αAmy8-sp-Apu-8U with SalI, blunt-ended, and inserted into the HindIII-digested and blunt-ended binary vector pSMY1H (Ho et al., 2000, supra) to generate, pGApu, pGpApu, pA3Apu and pA8Apu, respectively (FIG. 1).

Transformation

Plasmids pGApu, pGpApu, pA3Apu and pA8Apu, were respectively introduced into *Agrobacterium tumefaciens* strain EHA101 (Hood et al. (1986) J Bacteriol 168:1291–1301) with an electroporator (BTX) according to the manufacturer's instruction. Calli induced from immature rice seeds were co-cultured with Agrobacterium according to the methods described by Hiei et al. (1994, Plant J. 6:271–282) and Toki (1997, Plant Mol Biol Rep 15:16–21). Expression of APU in *E. coli* and Preparation of Polyclonal Antibodies The truncated Apu encoding amino acids 106 to 1060 was PCR-amplified using genomic DNA of *T. ethanolicus* 39E as template and oligonucleotides 5'-CGCATAT-GTTAAGCTTGCATCTTGATTC-3' (SEQ ID NO:12) as forward primer and 5'-CCGCTCGAGCTAC-ATATTTTCCCCTTGGCCA-3' (SEQ ID NO:13) as reverse primer. The amplified DNA fragment was digested with NdeI and XhoI and ligated into the same sites in pET20b(+) (Novagen) to generate pET-APU. pET-APU was transferred to *E. coli* strain BL21 (DE3) and APU was expressed. Purification of APU was performed according to the instruction provided by Novagen. One hundred micrograms of purified APU was injected into a New Zealand White rabbit successively at 4–6 week interval according to the methods described by Williams et al. (1995, Expression of foreign proteins in *E. coli* using plasmid vectors and purification of specific polyclonal antibodies, in: DNA Cloning 2-Expression Systems-A Practical approach. (Ed) Glover and Hames, IRL Press, New York).

In Situ Hybridization and Immunohistochemistry

Developing rice seeds were fixed in 3% paraformaldehyde and 0.25% glutaradehyde in 0.1 N phosphate buffer (PB) (pH 7.0) for 24 h at 4° C. After dehydration in a graded ethanol series, samples were embedded in Paraplast (Oxford Labware, St. Louis, Mo.) and sectioned at 10 mm with a rotary microtome. Sections were applied to slide glasses treated with 3-aminopropyltricholosilane (Shinetsu Chemicals, Tokyo, Japan). A digoxygenin-labeled sense and antisense RNA probes (~2865 bp) was prepared from the coding region of the Apu cDNA. Probes were degraded to a mean length of 200 bp by incubating in alkali at 60° C. for 43 min. In situ hybridization was performed as described in Kouchi and Hata (1993, Mol. Gen. Genet. 238:106–119). The hybridization signal was not detected when sense probe was used. Accordingly, only results obtained using the antisense probe are shown.

Tissue sections of developing rice seeds similarly prepared as described above were used for detection of APU using an immunohistochemistry method. After melting the paraffin on a hotplate, sections were dewaxed by incubation in xylene and 100–30% ethanol series ethanol in 0.1 N PB twice (10 min each). After a final wash in 0.1N PB for 10 min, the sections were blocked with 1% bovine serum albumin in PB for 30 min. After rinsing in PB, the tissues were incubated with the APU primary antibodies for 60 min at 25° C. and rinsed with PB. Detection of immunoreactivity was performed using the avidin-biotin-complex-method. Sections were incubated for 60 min with biotinylated goat anti-rabbit IgG (ABC-Kit, Vector Laboratories, Peterborough, UK) in PB at room temperature, extensively washed in PB for three times (10 min each), and finally incubated with the alkaline phosphatase coupled ABC (ABC-Kit, Vector Laboratories) for 30 min. After another washing with PB, alkaline phosphatase label was developed in a solution (100 mM Tris-HCl, 100 mM NaCl, 50 mM $MgCl_2$, pH 9.5) containing nitro-blue tertrazolium (NBT, 340 mg/ml, Boehinger Mannheim) and 5-brom-4-chloro-3-indolyl-phosphate (BCIP, 170 mg/ml, Boehinger Mannheim) for 2 h in the dark at 25° C. Color development was stopped by washing in water. APU was not detected when the pre-immune serum was used.

APU Activity Assay and Enzyme-Linked Immunosorbent Assay (ELISA)

Rice seeds or tissues were ground in liquid N2, lysed with a buffer (90.8 mM K2HPO4, 9.2 mM KH2PO4, 10 mM EDTA, 10% glycerol, 1% Triton X-100, and 7 mM b-mercaptoethanol) and centrifuged at 15,000 xg for 10 min and supernatant was collected. APU activity was assayed as described by Mathupala et al. (1993, J. Biol. Chem. 268:16332–16344). ELISA was performed as described by Ausubel et al. (1992, Short Protocols in Molecular Biology, 2nd ed., in: A Compendium of Methods from Current Protocols in Molecular Biology, John Wiley & Sons, New York). The total protein concentration was determined using a Bio-Rad protein assay kit based on the Bradford dye-binding assay.

Determination of Amylose Content

Amylose content in mature seeds was determined as described by Juliano (1971, Cereal Sci. Today 16:334–338). Serial dilution of purified amylose from potato (Sigma) was used as standards. The amylose content was determined using Technicon Autoanalyzer II (Bran+Luebbe, Norderstedt, Germany).

OTHER EMBODIMENTS

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

We claim:

1. A DNA construct comprising a seed-specific promoter operatively linked to a nucleotide sequence encoding a fragment of *Thermoanaerobacterium ethanolicus* amylopullulanase that comprises amino acids 106–1060 of SEQ ID NO:1 and is free of amino acids 1–105 and 1061–1481 SEQ ID NO:1.

2. The construct of claim 1, further comprising a nucleotide sequence encoding a signal peptide linked to the nucleotide sequence encoding the fragment of *Thermoanaerobacterium ethanolicus* amylopullulanase.

3. The construct of claim 2, wherein the signal peptide is a glutelin signal peptide.

4. The construct of claim 1, wherein the construct further includes a 3' gene terminator sequence.

5. The construct of claim 4, wherein the 3' gene terminator sequence is a nopaline synthase gene terminator sequence.

6. The construct of claim 1, wherein the seed specific promoter is a glutelin promoter or an α-Amy promoter.

7. The construct of claim 6, wherein the seed specific promoter is the α-Amy3 or the α-Amy8 promoter.

8. The construct of claim 6, wherein the seed specific promoter is the GluB promoter.

9. A genetically engineered seed, comprising a seed specific promoter operably linked to a nucleotide sequence encoding a fragment of *Thermoanaerobacterium ethanolicus* amylopullulanase that comprises amino acids 106–1060 of SEQ ID NO:1 and is free of amino acids 1–105 and 1061–1481 of SEQ ID NO:1.

10. The seed of claim 9, wherein the genetically engineered seed is a rice, corn, wheat, or barley seed.

11. The seed of claim 9, wherein the genetically engineered seed is a rice seed.

12. The seed of claim 9, wherein the nucleotide sequence encodes a signal peptide linked to the the fragment of *Thermoanaerobacterium ethanolicus* amylopullulanase.

13. The seed of claim 12, wherein the signal peptide is a glutelin signal peptide.

14. The seed of claim 9, wherein the nucleotide sequence further includes a 3' gene terminator sequence.

15. The seed of claim 14, wherein the 3' gene terminator sequence is a nopaline synthase gene terminator sequence.

16. The seed of claim 9, wherein the seed specific promoter is a glutelin promoter or an α-Amy promoter.

17. The seed of claim 16, wherein the seed specific promoter is the GluB promoter.

18. The seed of claim 16, wherein the seed specific promoter is the α-Amy3 or the αAmy8 promoter.

19. A method of producing seeds having a modified starch structure or content, comprising:

transforming a plant cell with a DNA construct comprising a seed specific promoter operatively linked to a nucleotide sequence encoding a fragment of *Thermoanaerobacterium ethanolicus* amylopullulanase that comprises amino acids 106–1060 of SEQ ID NO:1 and is free of amino acids 1–105 and 1061–1481 of SEQ ID NO:1;

generating a whole plant from the transformed plant cell;

optionally multiplying the whole plant; and harvesting seeds from the whole plant or multiplied whole plants.

20. The method of claim 19, wherein the plant cell is a rice cell.

21. A method of producing a starch having a modified structure, comprising:

transforming a plant cell with a DNA construct comprising a seed specific promoter operatively linked to a nucleotide sequence encoding a fragment of *Thermoanaerobacterium ethanolicus* amylopullulanase that comprises amino acids 106–1060 of SEQ ID NO:1 and is free of amino acids 1–105 and 1061–1481 of SEQ ID NO:1;

generating a whole plant from the transformed plant cell;

optionally multiplying the whole plant;

harvesting seeds from the whole plant or multiplied whole plants; and extracting the starch from the seeds.

22. The method of claim 21, wherein the plant cell is a rice cell.

23. A DNA construct comprising a seed-specific promoter operatively linked to a nucleotide sequence encoding an amino acid sequence consisting of amino acids 106–1060 of SEQ ID NO:1.

24. The construct of claim 23, further comprising a nucleotide sequence encoding a signal peptide linked to the nucleotide sequence encoding the fragment of SEQ ID NO:1.

25. The construct of claim 24, wherein the signal peptide is a glutelin signal peptide.

26. The construct of claim 23, wherein the seed specific promoter is a glutelin promoter or an α-Amy promoter.

27. The construct of claim 23, wherein the seed specific promoter is the α-Amy3 or the α-Amy8 promoter.

28. The construct of claim 23, the seed specific promoter is a GluB promoter.

29. A genetically engineered seed comprising the construct of claim 23.

30. A genetically engineered seed comprising the construct of claim 26.

31. The seed of claim 29, wherein the genetically engineered seed is a rice, corn, wheat, or barley seed.

32. A method of producing seeds having a modified starch structure or content, comprising:

transforming a plant cell with the construct of claim 23;

generating a whole plant from the transformed plant cell;

optionally multiplying the whole plant; and harvesting seeds from the whole plant or multiplied whole plants.

33. The method of claim 32, wherein the plant cell is a rice cell.

* * * * *